United States Patent [19]

Karpf

[11] Patent Number: 4,919,671
[45] Date of Patent: Apr. 24, 1990

[54] METAL ANCHORING PART FOR A KNEE JOINT ENDOPROSTHESIS

[75] Inventor: Kurt Karpf, Holderbank, Switzerland

[73] Assignee: Sulzer Brothers Limited, Winterthur, Switzerland

[21] Appl. No.: 181,079

[22] Filed: Apr. 13, 1988

[30] Foreign Application Priority Data

May 15, 1987 [CH] Switzerland ............ 1888/87

[51] Int. Cl.⁵ .................................. A61F 2/38
[52] U.S. Cl. ............................ 623/20; 623/18
[58] Field of Search .................. 623/20, 22, 23

[56] References Cited

U.S. PATENT DOCUMENTS

| 3,774,244 | 11/1973 | Walker. | |
|---|---|---|---|
| 4,158,684 | 6/1979 | Klawitter et al. | |
| 4,743,261 | 5/1988 | Epinette | 623/20 |

FOREIGN PATENT DOCUMENTS

| 0508686 | 1/1955 | Canada | 623/23 |
|---|---|---|---|
| 0135319 | 7/1984 | European Pat. Off. | |
| 3429157 | 8/1984 | Fed. Rep. of Germany. | |
| 2585236 | 1/1987 | France | 623/20 |
| 0925336 | 5/1982 | U.S.S.R. | 623/22 |

Primary Examiner—Richard J. Apley
Assistant Examiner—Stephanie L. Iantorno
Attorney, Agent, or Firm—Kenyon & Kenyon

[57] ABSTRACT

The metal anchoring part, in one embodiment, has a flat bearing surface to receive a synthetic tibial endoprosthesis part as well as a parallel tibial plateau from which anchoring rails project. The anchoring rails are slidably mounted within guide bores in a tibia to permit sliding of the anchoring part in the ventral/dorsal direction. In addition, a lock-like latch is provided in each rail to permit securement of the anchoring part in a tibia after placement. The anchoring part may be made as a half part for mounting on the medial or lateral part of a tibia or as a full part. A rotatable bolt may also be mounted in a pair of aligned rails to expand expandable rings secured to the tibial plateau for securing the part to the spongiosa of the tibia.

12 Claims, 3 Drawing Sheets

METAL ANCHORING PART FOR A KNEE JOINT ENDOPROSTHESIS

This invention relates to a metal anchoring part for a knee joint endoprosthesis. More particularly, this invention relates to a metal anchoring part for mounting in a tibia.

Heretofore, tibia parts of knee joint prostheses have usually been anchored in a tibia in a cement-free manner by means of pegs, such as described in European Patent Application 0151724, or by means of dowels, such as described in European Patent Application 0170779. In such cases, the pegs or dowels have been placed in bores which extend in the direction of the longitudinal axis of the tibia from the condylar surface in the bone. However, difficulties arise when using such tibia parts in only slightly destroyed knee joints which require only a partial replacement. That is, in such cases, the entire ligament system with two lateral and two crucial ligaments should be maintained with the intent that no ligament detachment need be undertaken during the surgical procedure. However, while the ligament system remains intact, the femur and tibia can only be displaced with respect to each other to a limited extent and may be drawn apart only in the direction of the longitudinal axis. Therefore, particularly on the tibia side, it has been difficult to form the bores required for a cement-free anchorage of a tibia part of an endoprosthesis in a tibia.

Accordingly, it is an object of the invention to be able to mount a tibia part of an endoprosthesis in a tibia in a simple manner without interrupting the ligament system of the knee joint It is another object of the invention to be able to mount a tibial component of an endoprosthesis in a simple manner with minimal trauma.

Briefly, the invention provides a metal anchoring part for a knee joint endoprosthesis which can be mounted in a prepared recess of a tibia for sliding in a ventral to dorsal direction. In this respect, the anchoring part has a tibial bearing surface on one side which functions as a support for a body of synthetic material In addition, the anchoring part has a tibial plateau on an opposite side from the bearing surface which is disposed in parallel relation relative to the bearing surface and to the ventral to dorsal direction. In addition, hollow anchoring rails extend from the plateau and are aligned in the ventral to dorsal direction in order to receive securing means for securing the anchoring part in a tibia In one embodiment, the anchoring part is constructed for mounting on one-half of a tibia and, in this respect, the tibial plateau extends on an inclined plane from the medial or lateral side to the center plane of the tibia. In another embodiment, for mounting across the tibia, the tibia plateau is formed of two surfaces which are disposed on inclined planes in symmetric relation to each other.

The construction of the anchoring part with surfaces which are parallel to each other and to the ventral to dorsal direction permits the anchoring part to be slid into a prepared tibia in the manner of a drawer sliding into a cabinet. Securement of the part within the tibia takes place by means of the anchoring rails.

Since the rails extend in the ventral to dorsal direction, all calibers and instruments may also be introduced into the tibia from the ventral to dorsal without the ligament system requiring touching or interruption.

In one embodiment, the anchoring rails are formed of circular cylindrical tubes which extend through the plane of the tibial plateau so as to define undercuts which prevent motion of the secured part in the direction of the longitudinal axis of the tibia.

The securing means used in a rail may be in the form of a shaft which is rotatably mounted eccentrically therein and which carries a plurality of cams for pivoting from a retracted position within the plane of the rail to an extended position projecting through the plane for penetrating into spongiosa. In this regard, the rail is provided with a plurality of slots aligned with the cams in order to permit the cams to extend therethrough into the spongiosa while at the same time limiting rotation of the shaft. In this embodiment, the anchoring part can be slid into place and then the shafts can be rotated to move the cams from the retracted positions into the extended positions in order to secure the part against movement within the tibia.

In another embodiment, the rails may be disposed in pairs in aligned relation in order to receive a rotatable bolt. In addition, a pair of expandable snap rings are secured to the tibial plateau in alignment with the rails to receive a conical threaded section of the bolt. In this case, upon rotation of the bolt, the expandable rings may be expanded into the surrounding spongiosa after the anchoring part has been positioned in place.

These and other objects and advantages of the invention will become more apparent from the following detailed description taken in conjunction with the accompanying drawing wherein.

Figure 1:
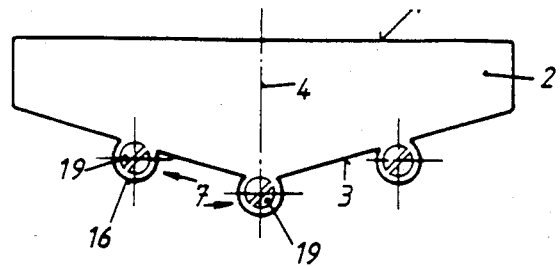
FIG. 1 illustrates a front view of a metal anchoring part constructed in accordance with the invention.

Referring to FIG. 1, the anchoring part 2 is in the form of a metal block having parallel boundary surfaces. As illustrated, the anchoring part 2 includes a tibial bearing surface 1 which acts as a foundation for a synthetic material body (not shown) which forms the actual bearing and sliding surface for a prosthesis of one or both femur condyles (not shown) This tibial bearing surface 1 which may function as a partial prosthesis for a replacement of the lateral or medial tibia sliding surface or can replace the entire tibial head extends essentially horizontally and is flat. In addition, the anchoring part 2 includes a tibia plateau 3 formed of a pair of surfaces disposed on inclined planes in symmetric relation to each other and to a center plane 4. As illustrated, each surface increases in the distal direction from the center plane 4 toward the medial and lateral edges.

Figure 2:
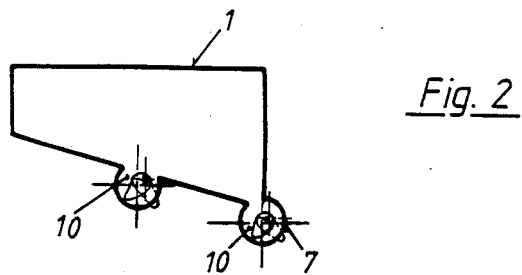
FIG. 2 illustrates a front view of a half-part constructed in accordance with the invention.
Figure 3:
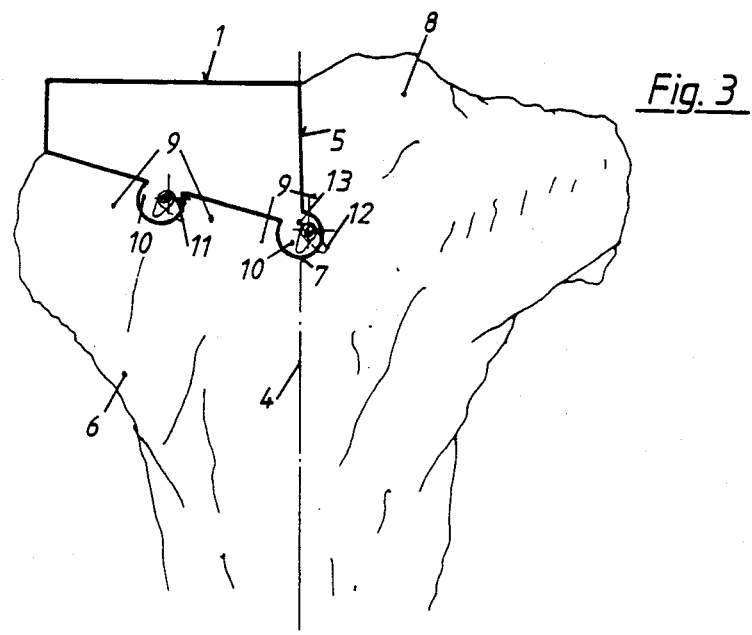
FIG. 3 illustrates a view of the half-part of FIG. 2 implanted in a tibia in accordance with the invention.
Figure 4:
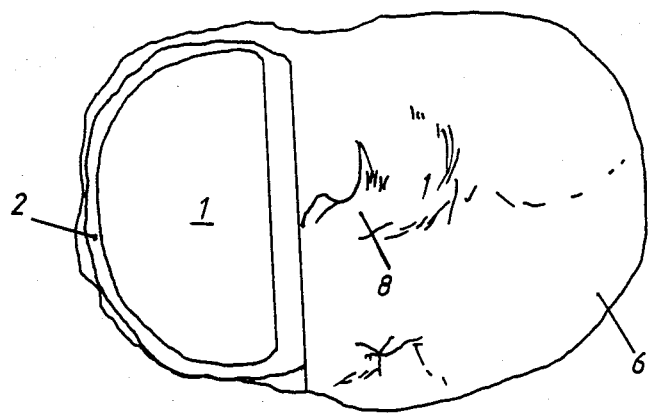
FIG. 4 illustrates a plane view of the half-part anchored in a tibia.

Referring to FIGS. 2 and 3, the anchoring part may be made as a half-part. In this respect, the half-part is sized so as to be used on the medial or lateral side of the tibia. For example, the part may be provided with a boundary wall 5 which extends along the center plane 4 to form an additional support surface which is braced in the surgically prepared tibia bone against an eminence 8. The boundary wall 5 may also serve as an anchoring surface into which bone tissue may grow, in the same manner as the plateau 3.

Figure 5:
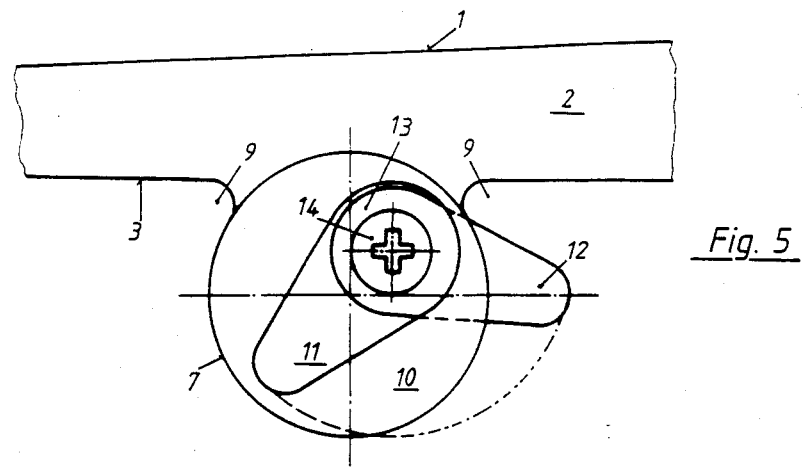
FIG. 5 illustrates an enlarged view of a securing means according to the invention; .

Referring to FIGS. 1, 3 and 5, each anchoring part is provided with hollow anchoring rails 7 which extend from the plateau 3 in the ventral to dorsal direction. These rails 7 permit the anchoring part to slide on the tibia head from ventral to dorsal in the manner of a drawer. To this end, the tibia is provided with suitable guides or "slide rails" to receive the rails 7.

As illustrated in FIG. 5, each rail 7 is formed as a circular cylindrical tube which extends into the plane of the tibia plateau 3. In this respect, the rail 7 is of a constant outer diameter along the entire length. Further, the rail 7 by extending through the plane of the tibial plateau 3 defines undercuts 9 which prevent a "lifting" of the anchoring part from the bone surface in the direction of the tibia axis.

Figure 6:
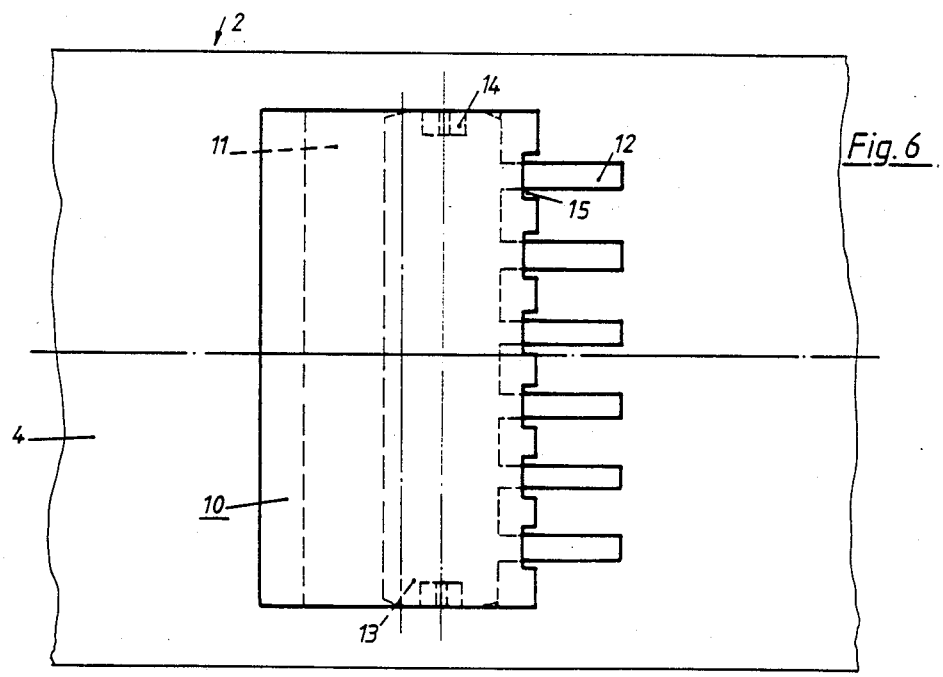
FIG. 6 illustrates a plan view of the securing means of FIG. 5.

As also indicated in FIG. 5, in order to secure the anchoring part 2 against opening, in the sense of a drawer, securing means are disposed in each rail 7. Each securing means is constructed in the manner of a safety lock-like latch. For example, each securing means includes a hollow cylinder 10 eccentrically within a bore 11 of the rail 7. In said cylinder 10 is rotatably mounted a shaft 13 which carries a plurality of cams 12 which can be pivoted from a retracted position within a plane of the rail 7 to an extended position projecting through the plane of the rail 7 for penetrating into spongiosa. As indicated, the bore 11 is of cam shape cross-section in order to accommodate reception of the cams 12. In addition, as indicated in FIG. 6, the rail 7 has a plurality of slots 15 aligned with the cams 12 to permit the cams 12 to extend therethrough while the ends of the slots limit rotation of the shaft.

Each end of the shaft is provided with a cross-head depression 14 for insertion of a key or suitable tool for turning of the shaft in order to rotate the shaft 13 and to move the cams 12 in the extended position by said rotation.

As indicated in FIG. 5, when the cams 12 are swung to the extended position, the cams 12 penetrate into soft spongiosa and, in this case, secure the anchoring part 2 against ventral/dorsal displacement.

Figure 7:
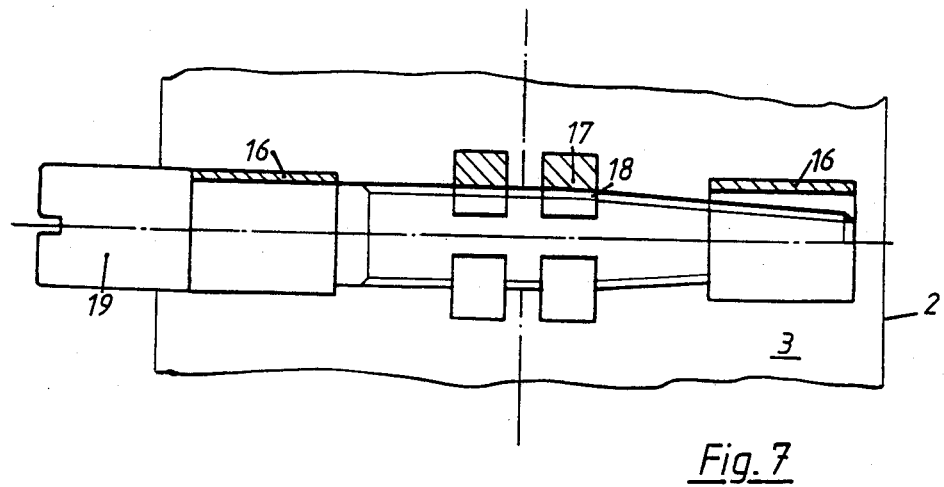
FIG. 7 illustrates a side view of a modified securing means in accordance with the invention.

Referring to FIGS. 1 and 7, the securing means may include a bolt 19 which is mounted within a pair of aligned rails 16, in the form of tubular sleeves. In addition, the bolt 19 has a conical threaded section between the sleeves 16 which is threadably fitted into a pair of expandable snap rings 17 secured to the tibial plateau 3 of the anchoring part 2 in alignment with the sleeves 16. Each ring 17 is provided with an internal thread 18 to threadably receive the conical part of the bolt 19 so that the rings expand outwardly into the spongiosa upon rotation of the bolt 19.

The sleeves 16 and snap rings 17 may be manufactured in one piece with the anchoring part 2. This has the advantage that difficulties of alignment which might occur upon a subsequent fastening, for example by welding, are obviated. However, a welding or soldering of the sleeves 16 and snap rings 17 to the anchoring part 2 is possible.

As illustrated in FIG. 1, the anchoring part 2 is provided with three rails 7 for securement purposes. In the half-anchoring part of FIG. 2, a pair of rails 7 is provided with one rail 7 being disposed on the axis of the boundary wall 5 so as to be disposed on the center plane 4 of the tibia as indicated in FIG. 3.

During implantation, the following procedure is recommended.

First, with appropriate instruments at the predetermined height and proper angle, anchoring bores or "slide rails" are drilled into the head of the tibia 6 in order to receive the anchoring rails 7. With a chisel, guided in the anchoring bores, excess bone material is subsequently removed. In addition, the anchoring bores above the equator thereof are cut so that a securing means may be inserted into the bore while being sufficiently guided on all sides.

The tibia 6 is provided with a recessed surface which is identical with the contact surface of the tibia head. In the case of the half-anchoring part, two support surfaces are available for the implant. For the anchoring part of FIG. 1, one large supporting surface is provided. In this respect, the two inclined surfaces of the tibia plateau 3 form an angle of from 75° to 110° with respect to each other. In addition, the transition from a large support surface to the nearly vertical surface at the edges may be formed as an edge or by means of a radius.

After the bores have been formed in the tibia 6, the anchoring part may be slid into place in the ventral/dorsal direction. Once properly positioned, the securing means may be actuated to secure the anchoring part in place. For example, with respect to the embodiment of FIG. 5, the shaft is rotated so as to position the cams 12 in the extended positions shown. In the embodiment of FIG. 7, the bolt 19 may be rotated so as to expand the snap rings 17.

The anchoring part may be made of any of the known metallic prosthesis materials. Further, the part may be cast or forged. Further, the contact surfaces toward the bone may be provided with a tissue-compatible coating or structure. The bearing surface opposite a metallic femur prosthesis may also be fashioned of polyethylene with the specifications customary for implants.

The anchoring part may also be used with a synthetic part which can be connected to the metal anchoring part during manufacture to form a unit which can then be supplied as a sterile implant. It is also possible to provide a polyethylene part and anchoring part with snaps or the like so that a final connection takes place during a surgical procedure.

The invention thus provides a metal anchoring part which can be implanted within a tibia without having to displace the ligament system of a knee joint.

Further, the invention provides an anchoring part which can be secured within a tibia by mechanical means as well as by boundary surfaces into which bone tissue may grow in order to provide a secure support for a tibial component of a knee joint endoprosthesis.

What is claimed is:

1. A metal anchoring part for a knee joint endoprosthesis having a tibia bearing surface on one side, a tibial plateau on an opposite side from said bearing surface and disposed on an inclined plane and hollow anchoring rails extending from said plateau in a ventral to dorsal direction to permit sliding in said direction relative to a prepared recess in a tibia.

2. A metal anchoring part as set forth in claim 1 wherein each rail is a circular cylindrical tube extending through said plane.

3. A metal anchoring part for a knee joint endoprosthesis having a tibial bearing surface on one side, a tibial plateau on an opposite side from said bearing surface and having a pair of surfaces disposed on inclined planes in symmetric relation to each other and hollow anchoring rails extending from said plateau surfaces in a ventral to dorsal direction to permit sliding in said direction relative to a prepared recess in a tibia.

4. In combination
   a metal anchoring part for a knee joint endoprosthesis having a tibial bearing surface on one side, a tibial plateau on an opposite side from said bearing surface and hollow anchoring rails extending from said plateau and aligned in a ventral to dorsal direction; and
   securing means disposed in said rails for securing said anchoring part in a tibia.

5. The combination as set forth in claim 4 wherein said means includes at least one shaft rotatably mounted eccentrically within one of said rails, and a plurality of cams mounted on said shaft for pivoting from a retracted position projecting through said plane for penetrating into spongiosa.

6. The combination as set forth in claim 5 wherein said one rail has a plurality of slots aligned with said cams to permit said cams to extend therethrough while limiting rotation of said shaft.

7. The combination as set forth in claim 4 wherein said securing means includes at least one bolt mounted within a pair of aligned rails and having a conical threaded section between said pair of rails, a pair of expandable snap rings secured to said tibial plateau in alignment with said pair of rails, said rings threadably receiving said conical section of said bolt whereby said rings are expandable into surrounding spongiosa upon rotation of said bolt.

8. The combination as set forth in claim 4 wherein each rail is of cylindrical shape and extends through a plane of said tibial plateau to define undercuts therewith.

9. The combination as set forth in claim 4 wherein said tibial plateau is disposed on an inclined plane relative to said tibial bearing surface.

10. The combination as set forth in claim 4 wherein said tibial plateau has a pair of surfaces disposed on inclined planes in symmetric relation to each other.

11. The combination as set forth in claim 4 wherein said bearing surface and said plateau are disposed in parallel relative to said ventral to dorsal direction to permit sliding in said direction relative to a prepared recess in a tibia.

12. The combination as set forth in claim 11 wherein said bearing surface is flat.

* * * * *

UNITED STATES PATENT AND TRADEMARK OFFICE
CERTIFICATE OF CORRECTION

PATENT NO. : 4,919,671

DATED : April 24, 1990

INVENTOR(S) : KURT KARPF

It is certified that error appears in the above-identified patent and that said Letters Patent is hereby corrected as shown below:

Column 5, line 17 after "position" insert --within a plane of said one rail to an extended position--

Signed and Sealed this

Seventeenth Day of September, 1991

Attest:

HARRY F. MANBECK, JR.

Attesting Officer

Commissioner of Patents and Trademarks